United States Patent
Daly

(10) Patent No.: US 9,867,813 B2
(45) Date of Patent: Jan. 16, 2018

(54) AMINOPYRIDINE BASED BUFFERS WITH WIDE BUFFERING RANGES, ANTIBIOTICS AND MYELIN DISEASE THERAPY

(71) Applicant: Thomas Daly, Arlington Heights, IL (US)

(72) Inventor: Thomas Daly, Arlington Heights, IL (US)

( * ) Notice: Subject to any disclaimer, the term of this patent is extended or adjusted under 35 U.S.C. 154(b) by 0 days.

(21) Appl. No.: 15/352,848

(22) Filed: Nov. 16, 2016

(65) Prior Publication Data
US 2017/0135998 A1    May 18, 2017

Related U.S. Application Data

(60) Provisional application No. 62/256,202, filed on Nov. 17, 2015.

(51) Int. Cl.
*A61K 31/437*    (2006.01)
*A61K 31/444*    (2006.01)
*C07D 401/12*    (2006.01)

(52) U.S. Cl.
CPC .......... *A61K 31/444* (2013.01); *A61K 31/437* (2013.01); *C07D 401/12* (2013.01)

(58) Field of Classification Search
CPC .......................... A61K 31/437; A61K 31/444
See application file for complete search history.

(56) References Cited

PUBLICATIONS

Gagliardi & Haas, 147 Fresenius Zeitschrift Fuer Analyticsche Chemie 321-6 (1955).*
Shah & Jones, 47 J. Am. Pharm. Assoc. 399-401 (1958).*

\* cited by examiner

*Primary Examiner* — Timothy R Rozof
(74) *Attorney, Agent, or Firm* — Clifford H. Kraft

(57) ABSTRACT

Amines and amine derivatives that improve the buffering range, and/or reduce the chelation and other negative interactions of the buffer and the system to be buffered. Aminopyridines channel blocking, combined with buffering and zwitterionic charge states make promising therapies for myelin diseases and as antibiotics.

9 Claims, 20 Drawing Sheets

G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. X, Y, and Z are independently chosen from either C or N.

G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH.

n is a non-negative integer. X,Y, and Z are independently chosen from either C or N.

n is a non-negative integer.

X, Y, and Z are independently chosen from either C or N.

X,Y, and Z are independently chosen from either C or N. R is -H, or alkyl, linear or branched, saturated or unsaturated, cylic or acyclic. from 1 to 22 carbons A, D and E are independantly chosen from -H, -CH3, -CH2CH3, -CH2CH2CH3, -CH2OH, -CH2OCS2H, -CH2COOH, -CH2CH2COOH, -CH2CH(CH3)COOH, -CH2PO(OH)2. G is chosen from -H, -CH3, -CH2CH3, -OH. X, Y, and Z are independently chosen from either C or N.

A, D and E are independantly chosen from -H, -CH3, -CH2CH3, -CH2CH2CH3, -CH2OH, -CH2OCS2H, -CH2COOH, -CH2CH2COOH, -CH2CH(CH3)COOH, -CH2PO(OH)2. G is chosen from -H, -CH3, -CH2CH3, -OH.

X,Y, and Z are independently chosen from either C or N.

X, Y, and Z are independently chosen from either C or N.

A, D and E are independantly chosen from -H, -CH3, -CH2CH3, -CH2CH2CH3, -CH2OH, -CH2OCS2H, -CH2OCS2H, -CH2COOH, -CH2CH2COOH, -CH2CH(CH3)COOH, -CH2PO(OH)2. G is chosen from -H, -CH3, -CH2CH3, -OH. X,Y, and Z are independently chosen from C or N.

A, D and E are independantly chosen from -H, -CH3, -CH2CH3, -CH2CH2CH3, -CH2OH, -CH2OCS2H, -CH2OCS2H, -CH2COOH, -CH2CH2COOH, -CH2CH(CH3)COOH, -CH2PO(OH)2. G is chosen from -H, -CH3, -CH2CH3, -OH.

X, X', Y, Y', and Z, Z' are independently chosen from C or N.

AMINOPYRIDINE BASED BUFFERS WITH WIDE BUFFERING RANGES, ANTIBIOTICS AND MYELIN DISEASE THERAPY This application is related to, and claims priority from, U.S. Provisional Patent Application No. 62/256,202 filed Nov. 17, 2015. Application 62/256,202 is hereby incorporated by reference in its entirety.

BACKGROUND

Field of the Invention

The present invention relates generally to the field of pyridine amines and more particularly to a classes of pyridine amines used as buffers in biological systems.

Description of the Problem Solved by the Invention

Amines are very useful compounds in the buffering of biological systems. Each class of amine has various limitations which require choosing an amine based on multiple factors to select the best amine. For example, pH buffering range is typically most important, but issues of chelation, and pH range stability, and solubility also come into play. Additionally, buffers interact with the biological system beyond simple buffering. The pyridine amines function to complex with cations in addition to buffering. This property can be exploited to assist in pharmacological delivery systems, or as active pharmaceutical ingredients themselves.

SUMMARY OF THE INVENTION

The present invention relates to amines and amine derivatives that improve the buffering range, and/or contribute to chelation. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability. These compounds also act as effective Myelin disease therapy agents and as antibiotics.

DESCRIPTION OF THE FIGURES

Attention is now directed to the following figures that describe embodiments of the present invention.

Figure 1A:
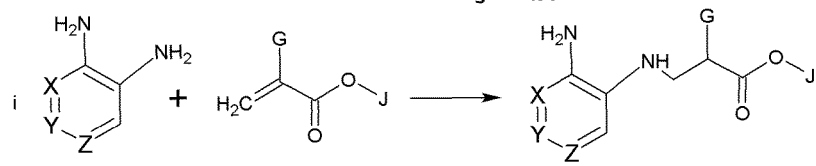
FIGS. 1A-1B teach the synthesis of zwitterionic buffers derived from 3,4-aminopyridine.
Figure 1A:
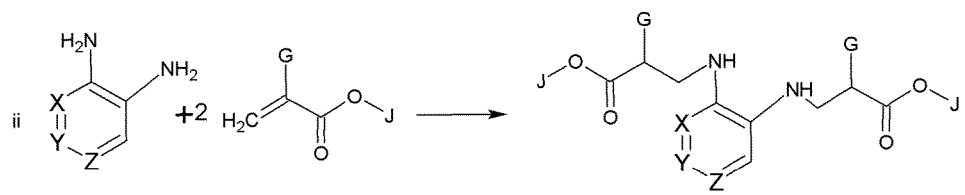
Figure 1A:
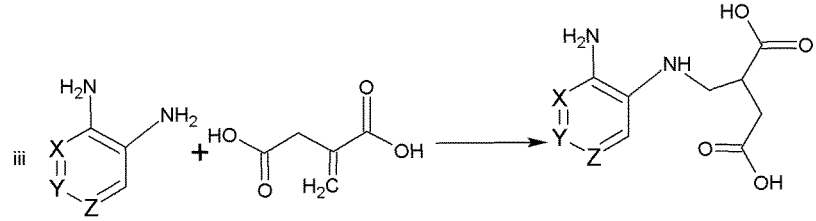
Figure 1A:
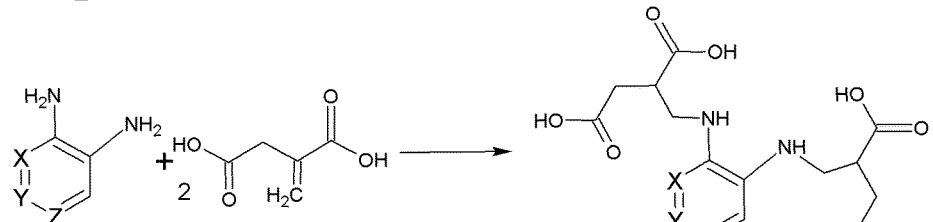
Figure 1A:
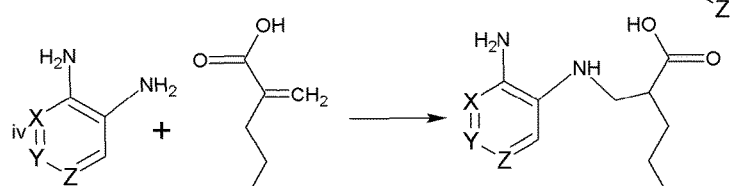
Figure 1A:
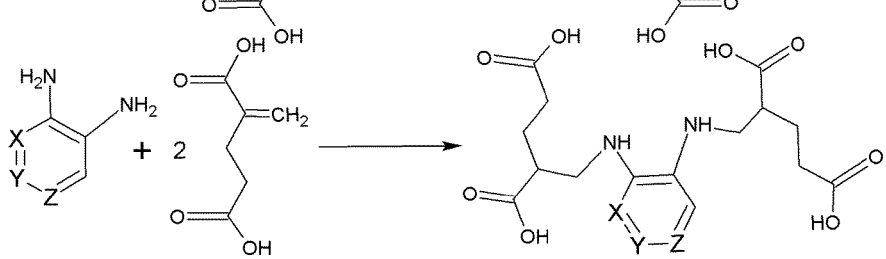
Figure 1B:
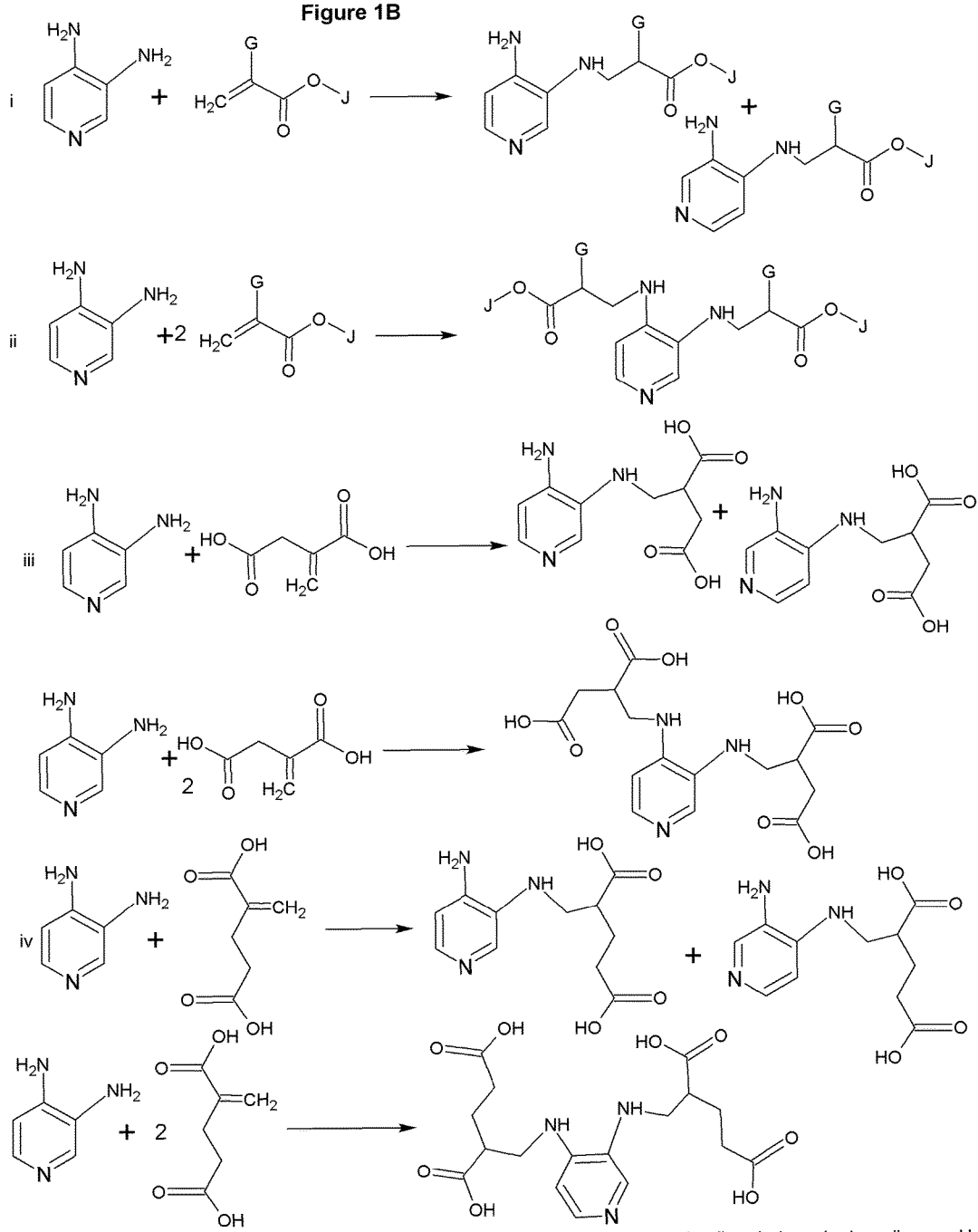
Figure 2A:
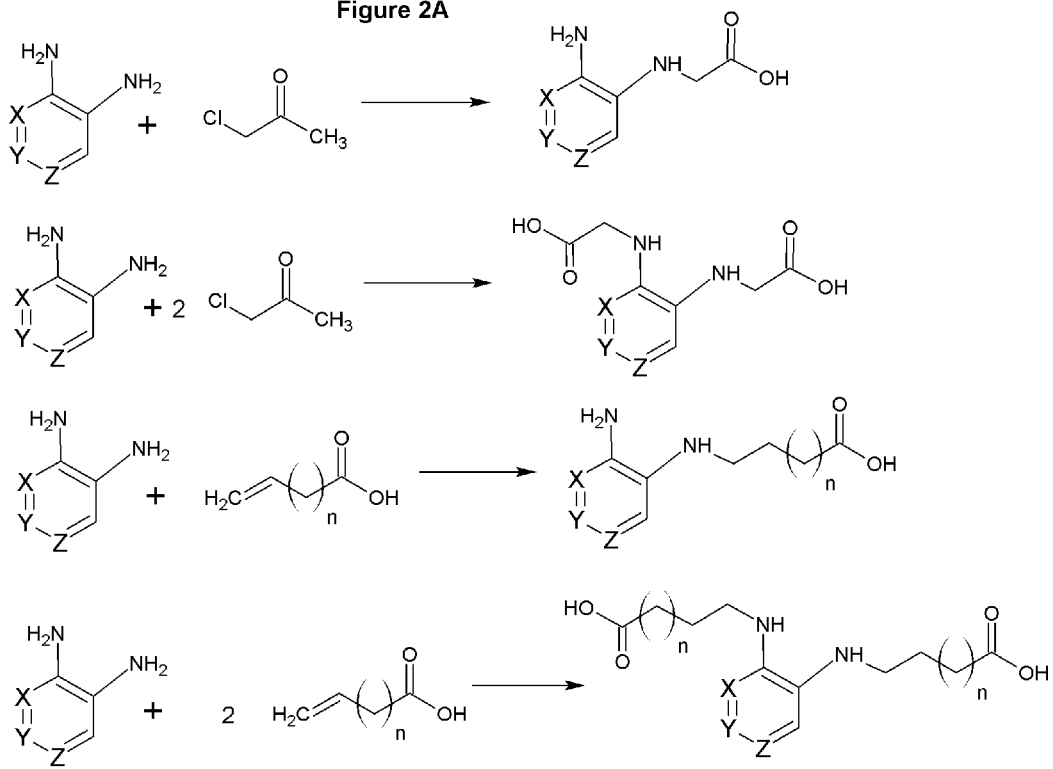
FIGS. 2A-2B show the derivation of zwitterionic buffers based on monochloroacetic acid and longer chain acrylates.
Figure 2B:
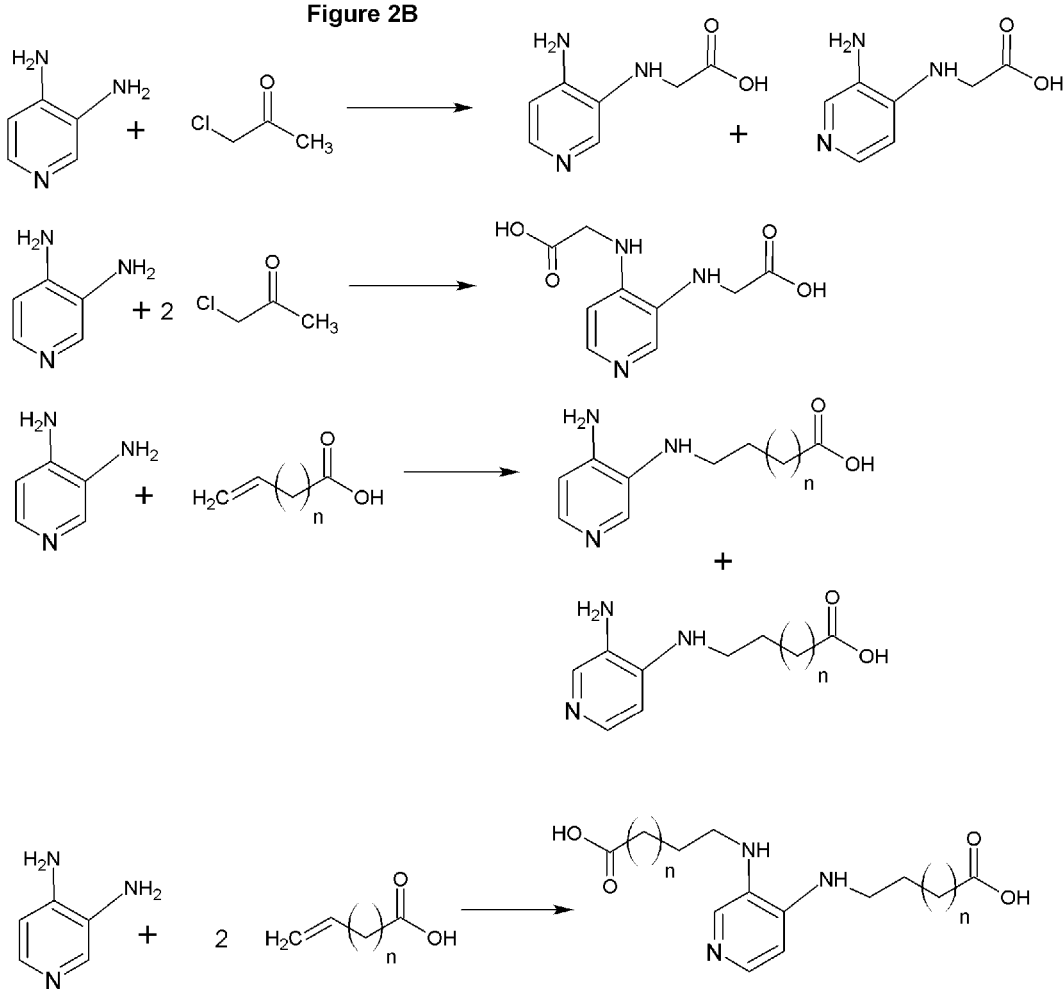

Several drawings and illustrations have been presented to aid in understanding the invention. The scope of the present invention is not limited to what is shown in the figures.

DETAILED DESCRIPTION OF THE INVENTION

Combining amines with monochloroacetic acid (MCA) or sodium vinyl sulfonate (SVS) results in products are zwitterionic buffers that can buffer in both acidic and basic pH conditions. A limited number amines are currently used for this purpose, such as, tromethamine and ammonia. The reaction of amines, alcohols, and aminoalcohols with acrylonitrile (via the Michaels Addition), followed by reduction results in amines and polyamines that have a broad buffering range. The further derivatization of the amines and polyamines with MCA and SVS yields a further crop of amine buffers with desirable properties. One skilled in the art will recognize that MCA and sodium monochloroacetic acid (SMCA) can be used interchangeably. Furthermore, the buffers taught herein, and their pharmacologically acceptable salts, act as potassium channel blockers and many will behave as MAOI, monoamine oxidase inhibitors, making them potential therapeutic agents for demyelinating diseases, Alzheimer's disease, Parkinson's disease, multiple sclerosis, and other neurological disorders such as ALS, and as antibiotics. The invention is particularly useful for myelin disease therapy. Furthermore, several molecules taught here as part of this invention are expected to promote the formation of astrocytes. Astrocytes are a key component of maintaining function and healing of spinal cord injuries, particularly those that result in a less than complete severing of the spinal cord, but that result in a removal of myelin from part of the neuron. In this case, the potassium ions that propagate the action potential are able to leak out of the neuron. The use of a potassium channel blocker, such as those taught here, along with an astrocyte promoter greatly improves neural function.

FIGS. 1A-1B and 2A-2B teach the synthesis of zwitterionic buffers of 3,4-diaminopyridine. Line i teaches the synthesis of a mono substitution on only one primary amino group. Line ii teaches the synthesis where each primary amino group is mono-substituted to the secondary amine. By utilizing HCl and methanol as the reaction media, the tertiary amines can be formed. The tertiary amines are simply the form where each primary amine group is disubstituted. The Michael addition products need not be symmetric, where the Michael adduct is all the same. The additions can be sequentially to make asymmetric products. The order of addition is such that one primary amino group reacts with the Michael adduct, then the second primary amine. Adding HCl and methanol, then adding a third equivalent of a Michael adduct will form a tertiary amine to one of the original primary amines, and finally the last amino hydrogen will react to from the only tertiary amine containing product. While not generally explicitly shown in subsequent figures, this principle holds throughout the invention disclosure.

Figure 3A:
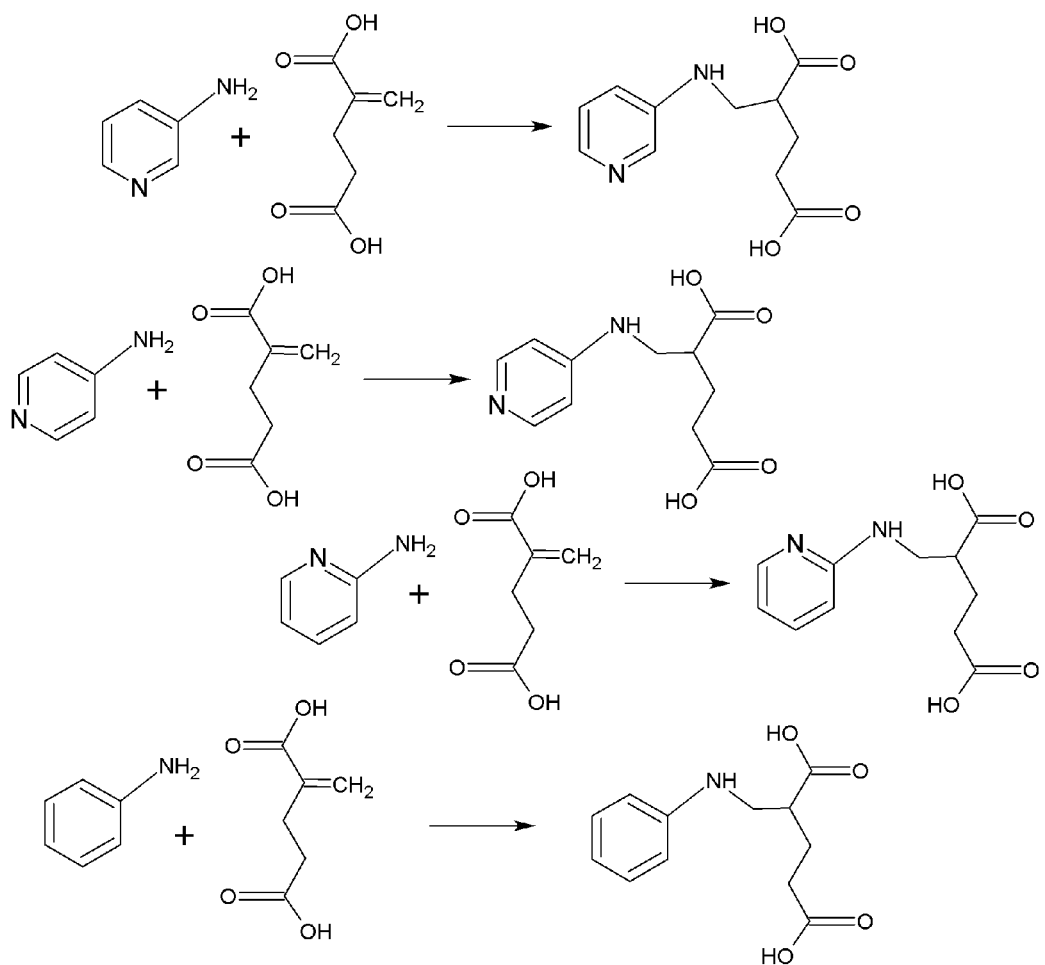
FIGS. 3A-3B teach the derivation of zwitterionic buffers from 2-aminopyridine, 3-aminopyridine, and 4-aminopyridine and aniline with 2-methyleneglutaric acid.
Figure 3B:
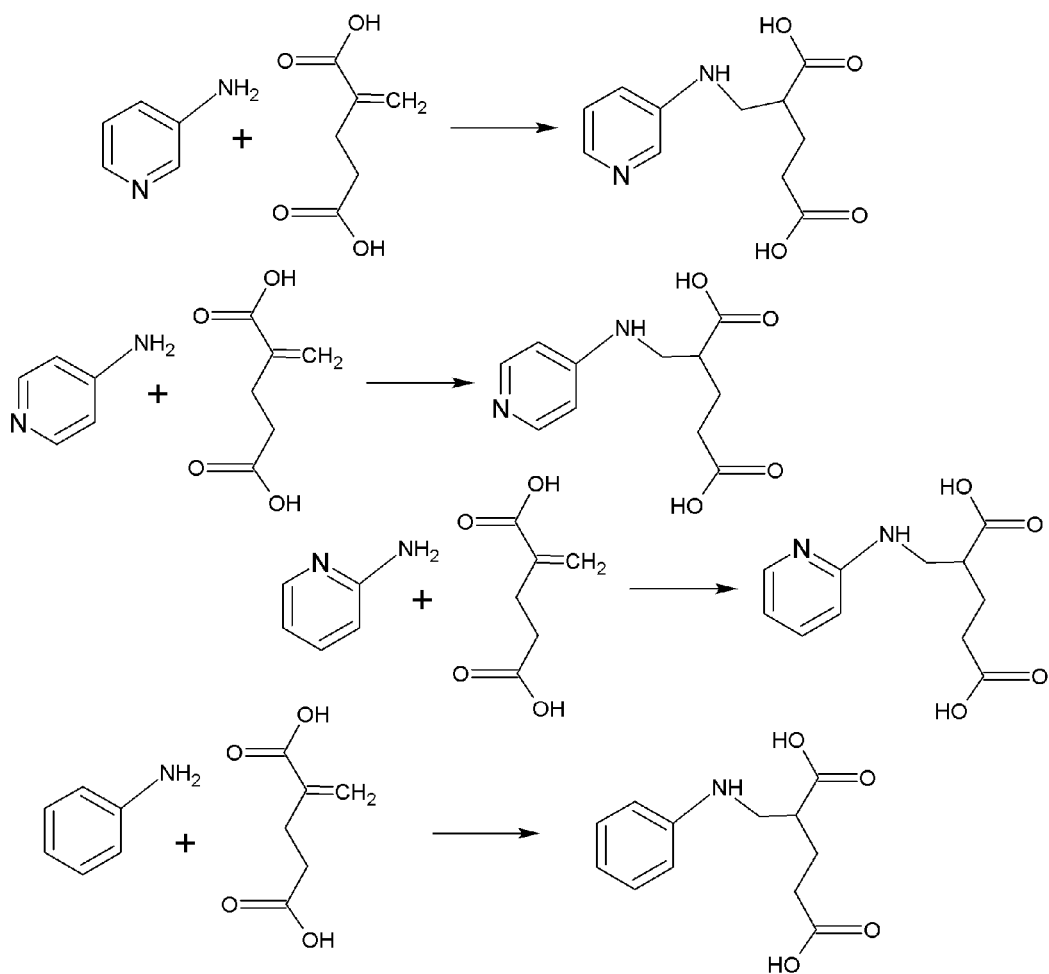
Figure 4A:
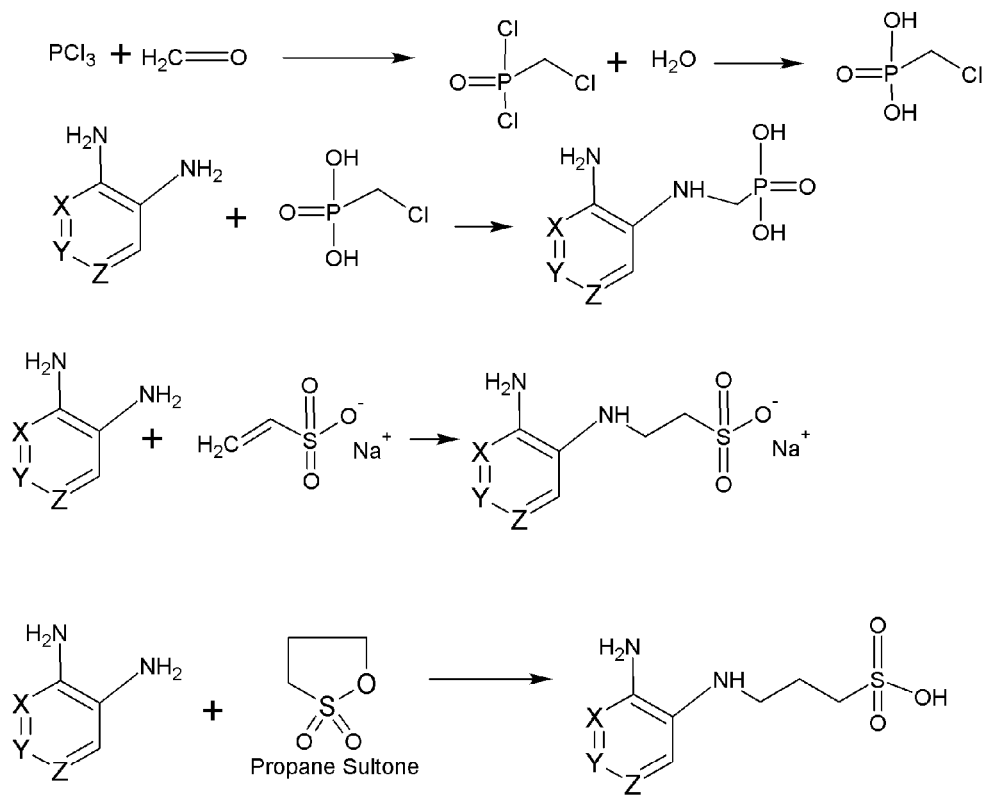
FIGS. 4A-4B teach synthesis of phosphonates and sulfonates from 3,4-aminopyridine.
Figure 4B:
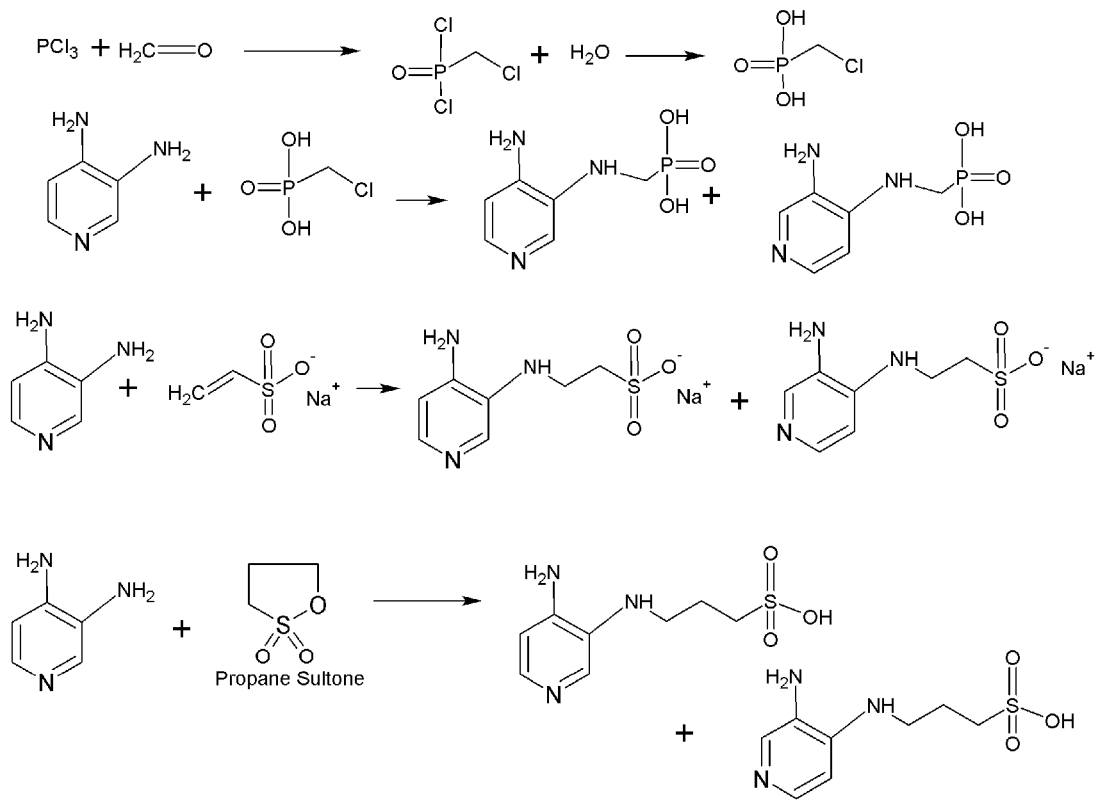

FIGS. 3A-3B teach the zwitterionic buffers of aminopyridines and 2-methyleneglutaric acid. These products act as potassium channel blockers, but are also expected to promote the generation of astrocytes, and thus greater neurological function. FIGS. 4A-4B teach the synthesis of phosphonate and sulfonate buffers. As before, the figures only show the 1:1 molar reaction, but both reactive sites on the two primary amines may be reacted, yielding up to four sites. The simplest beyond the single mono substituted products are the di-substituted products where each amine group undergoes one addition to form the secondary amine. For the propane sultone product, the higher sultone analogs, such as butyl sultone are part of this invention as well.

Figure 5A:
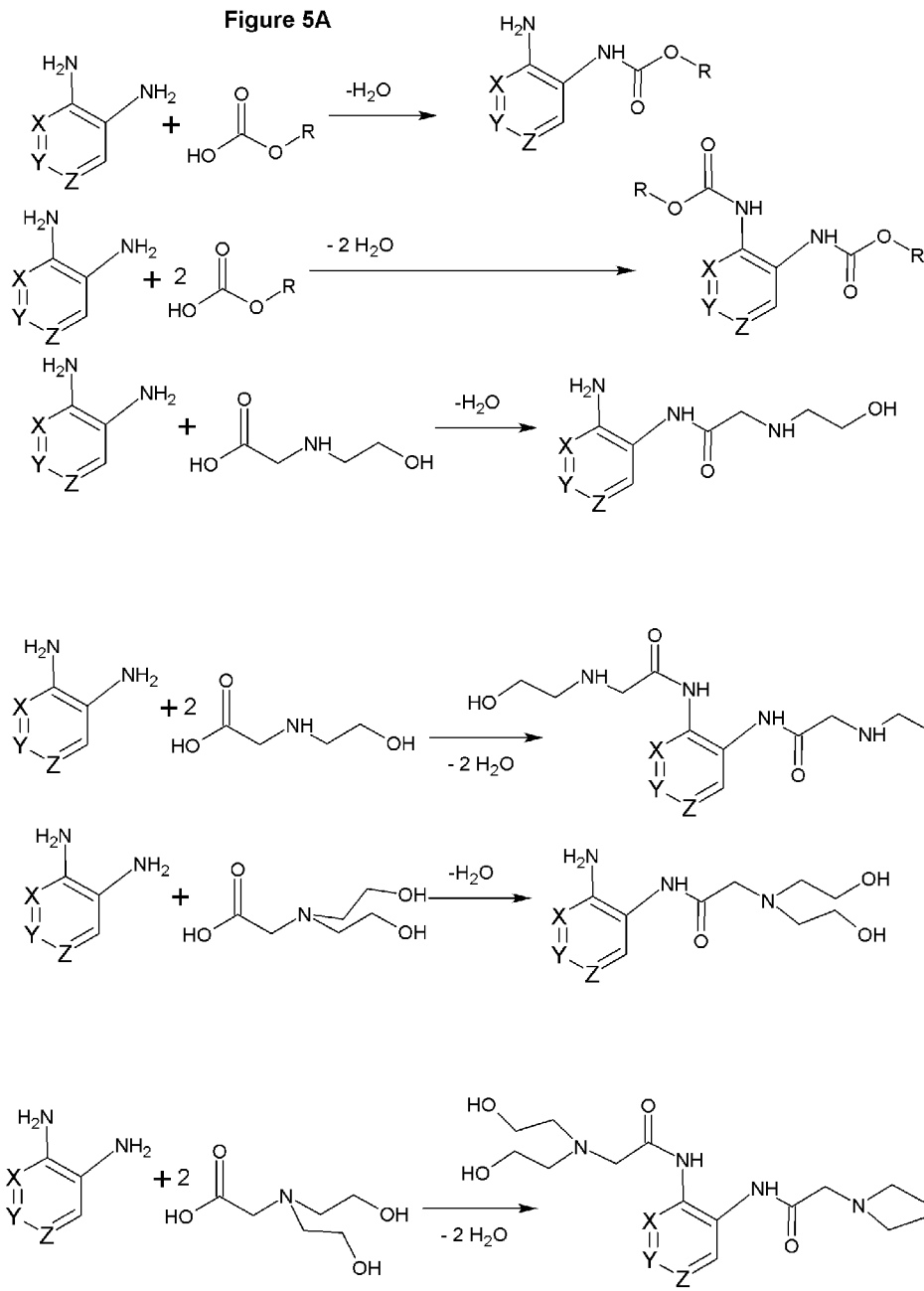
FIGS. 5A-5B and FIGS. 6A-6B show the synthesis of amides and carbamates from 3,4-aminopyridine.
Figure 5B:
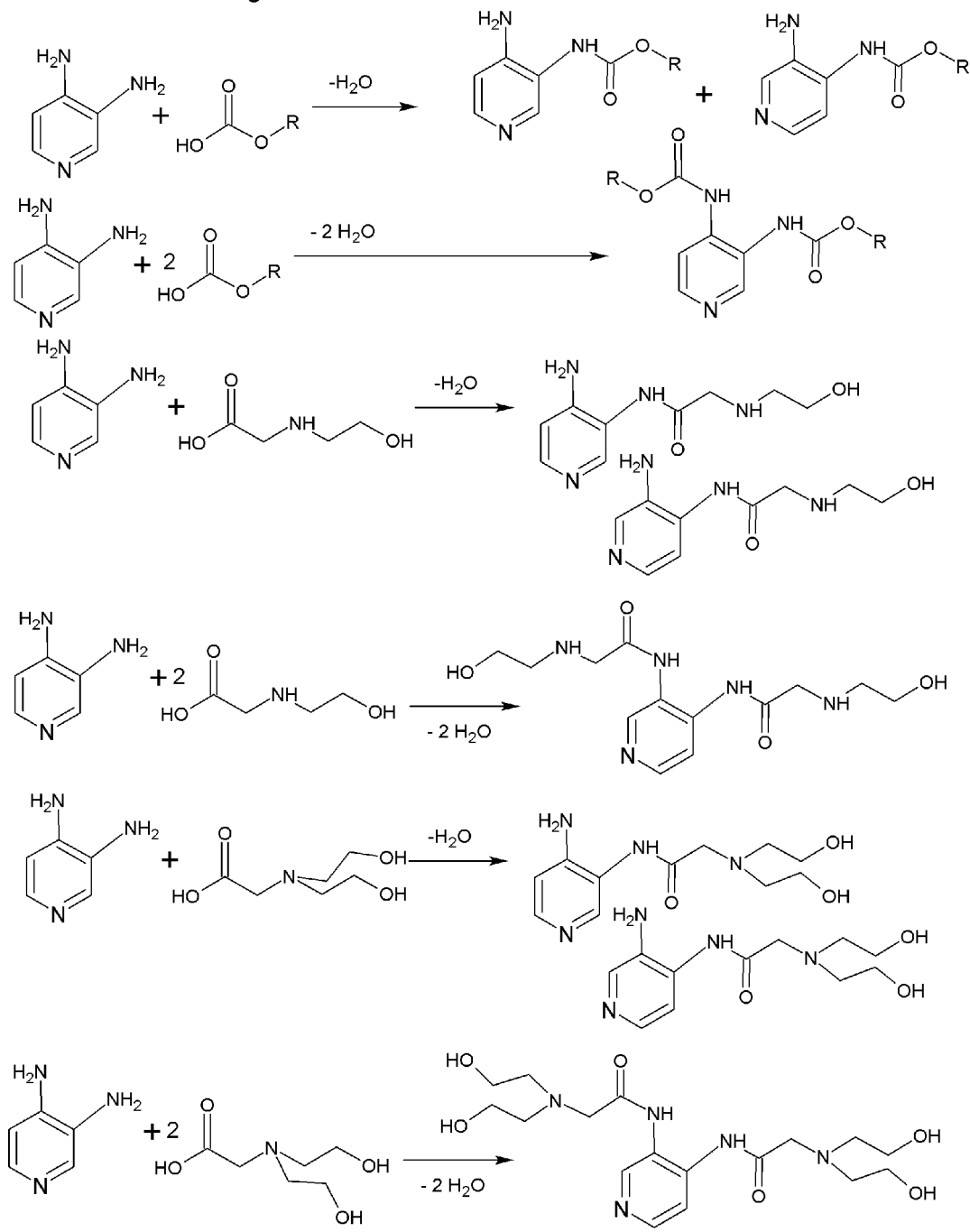
Figure 6A:
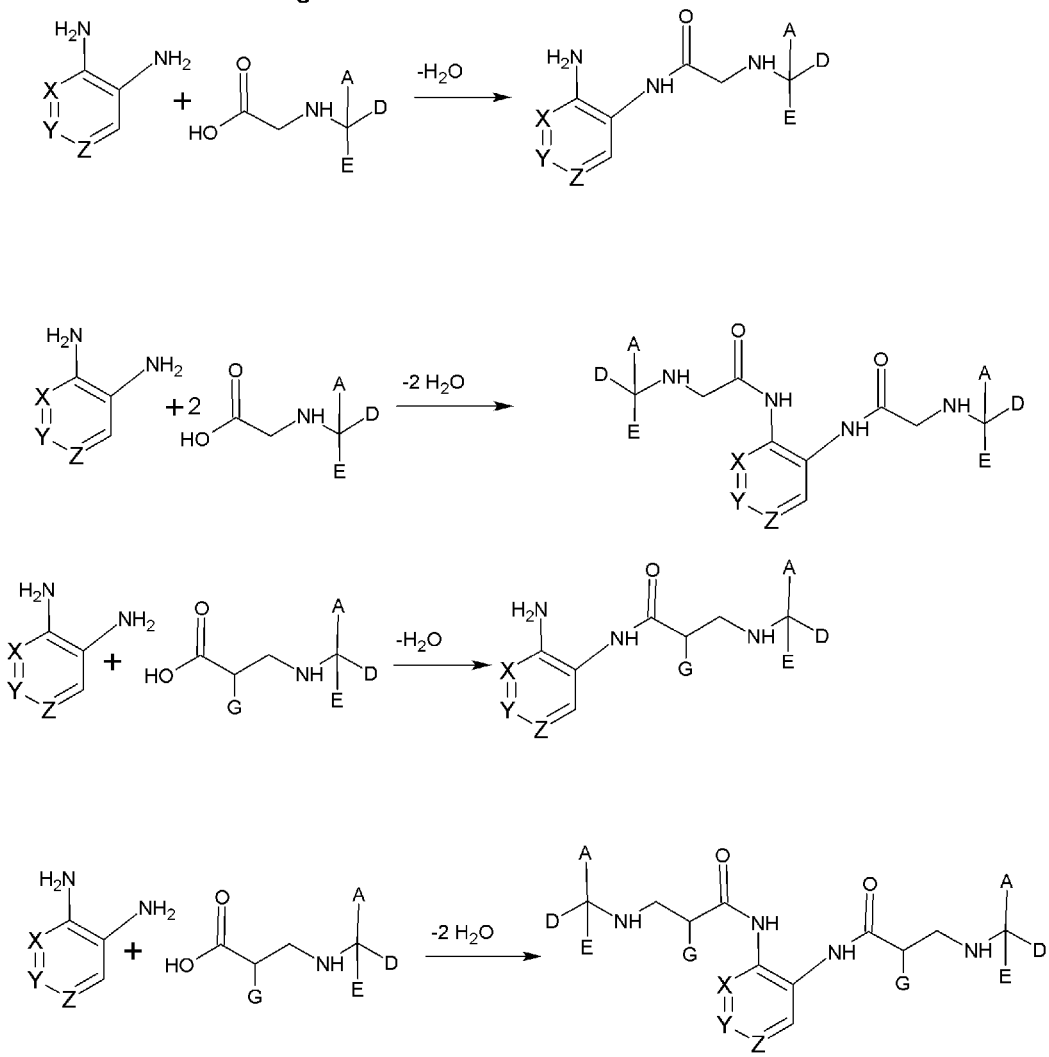
Figure 6B:
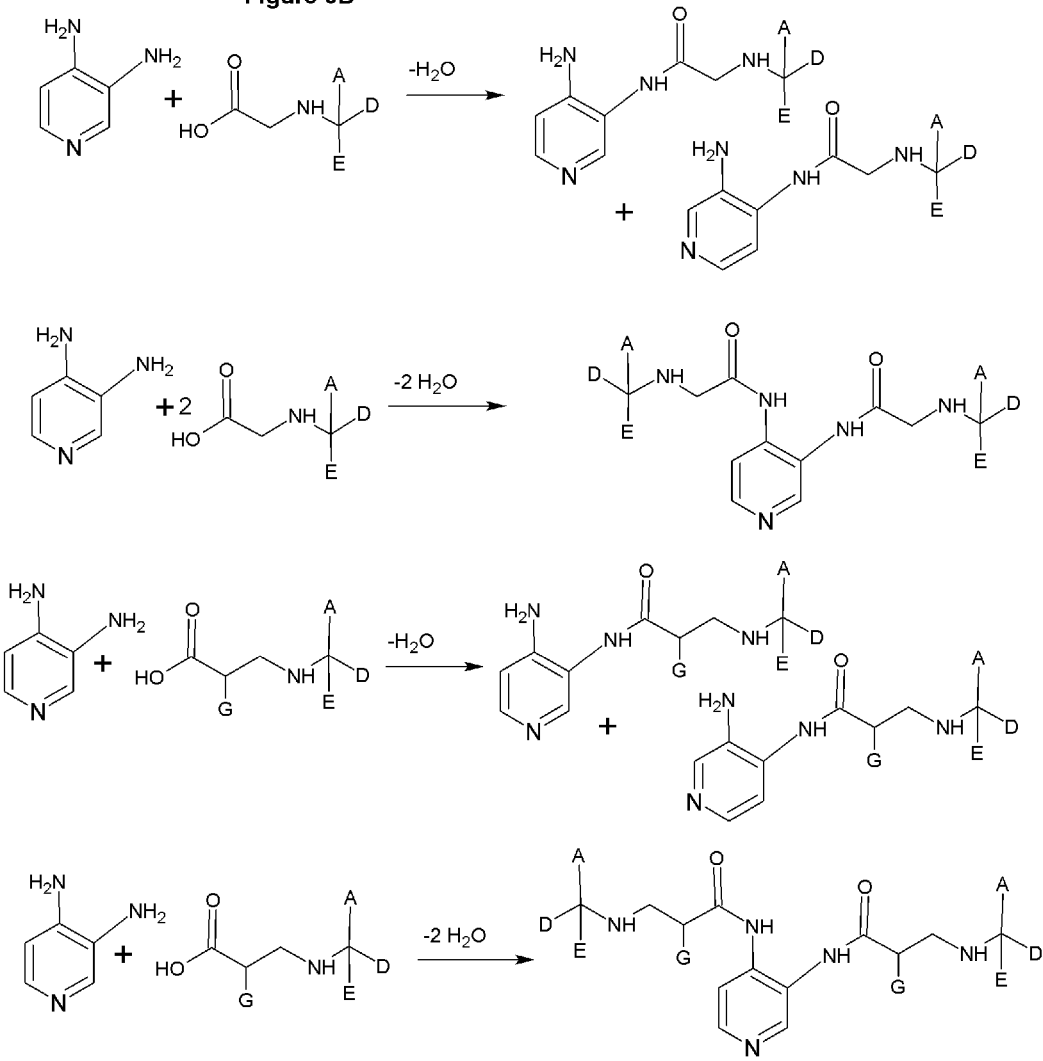
Figure 7A:
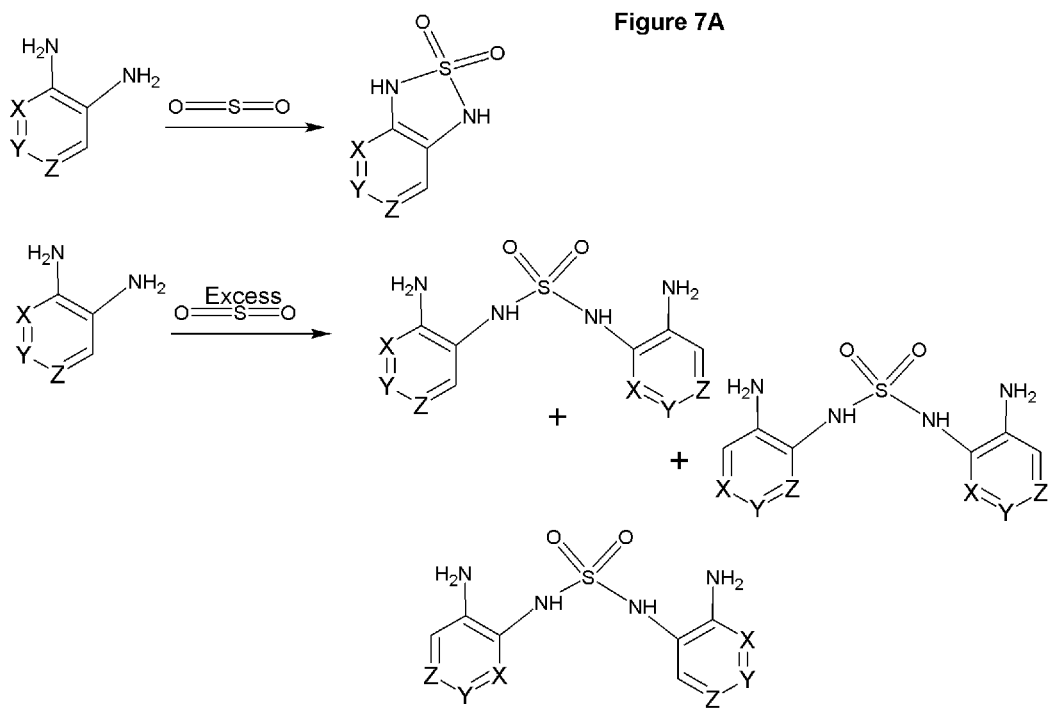
FIGS. 7A-7B teach the synthesis of sulfonamides from 3,4-aminopyridine.
Figure 7B:
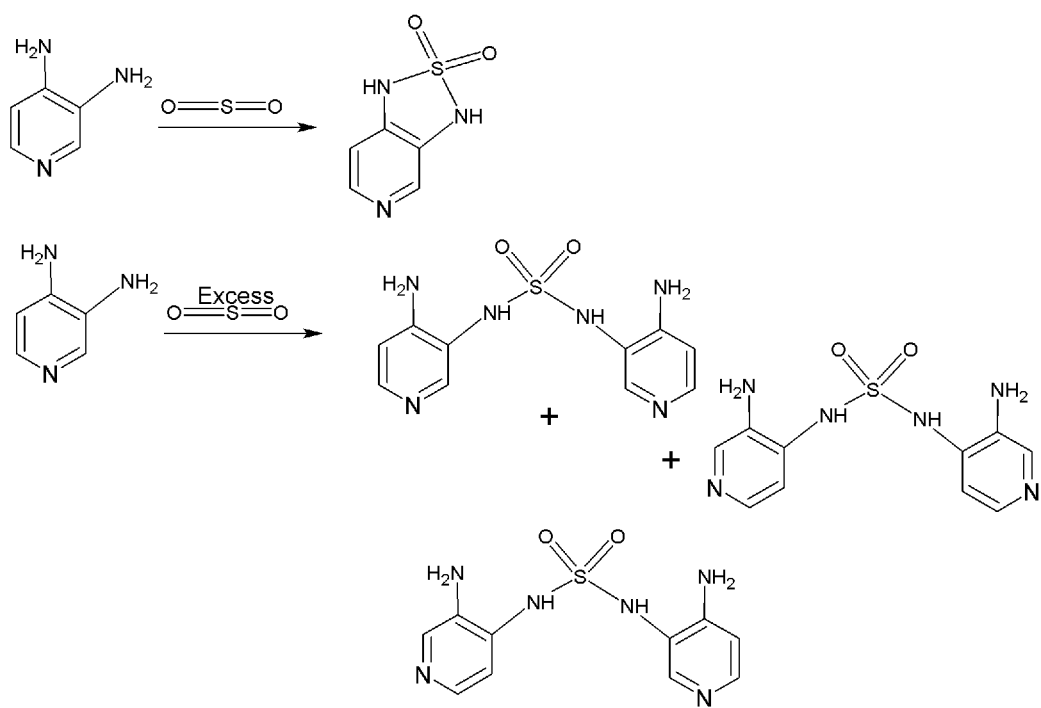

FIGS. 5A-5B teach the synthesis of amides and carbamates that are useful as potassium channel blockers. Monethanol amine and diethanolamine analogues are taught and shown as symmetric additions. This need not be the case. Asymmetric additions are part of this invention. FIGS. 6A-6B expand on FIGS. 5A-5B to include a wider range of amides and carbamates. Again, while the figure shows a symmetric addition, asymmetric additions, where the constituent groups, A, D, E are not the same for the differnt nitrogens, are within the scope of this invention. FIGS. 7A-7b teach the synthesis of sulfamides based in 3,4-aminopyridine.

Figure 8A:
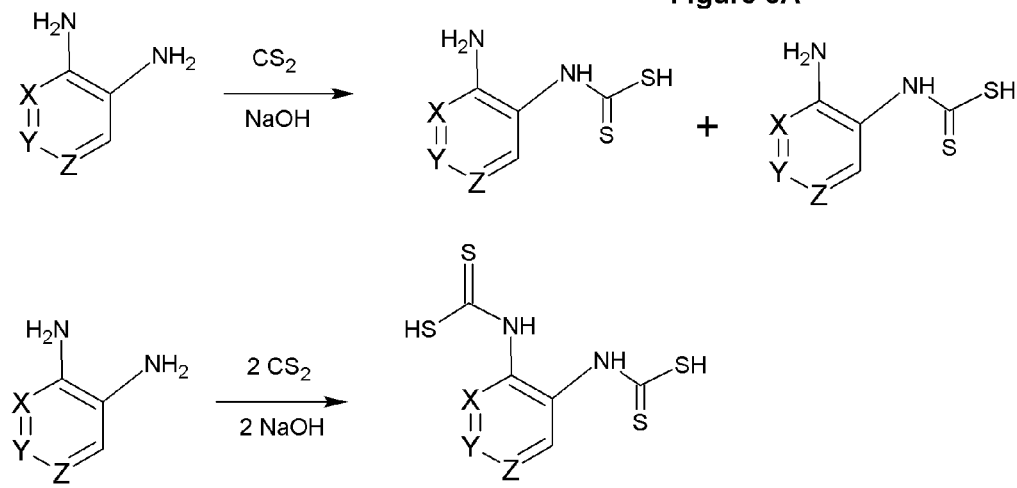
FIGS. 8A-8B teach the synthesis of dithiocarbamates from 3,4-aminopyridine.
Figure 8B:
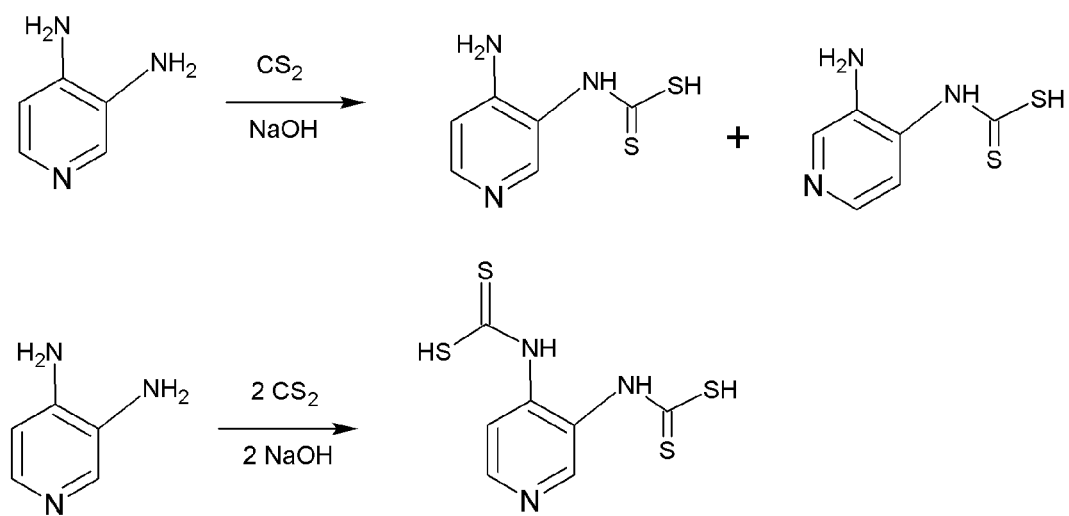

FIGS. 8A-8B teach the synthesis of dithiocarbamates based on 3,4-aminopyridine. While caustic is shown as the basicity agent, any other basicity agent may be used, including, but not limited to other mineral bases, such as KOH, and tertiary amines. methyldicoco amine is particularly useful as the resulting product exhibits much greater antimicrobial properties than the sodium or potassium derived forms. This is particularly interesting in agriculture and the methyldicoco amine acts as an adjuvant as well. The figures show the dithiocarbamates as free molecules, however, the free molecules are not stable and must be made and stored as the salts. The representation as free molecules and not salts is to simplify the structure and to not limit the invention to any particular salt. One skilled in the art will recognize all salts as part of the invention.

Figure 9A:
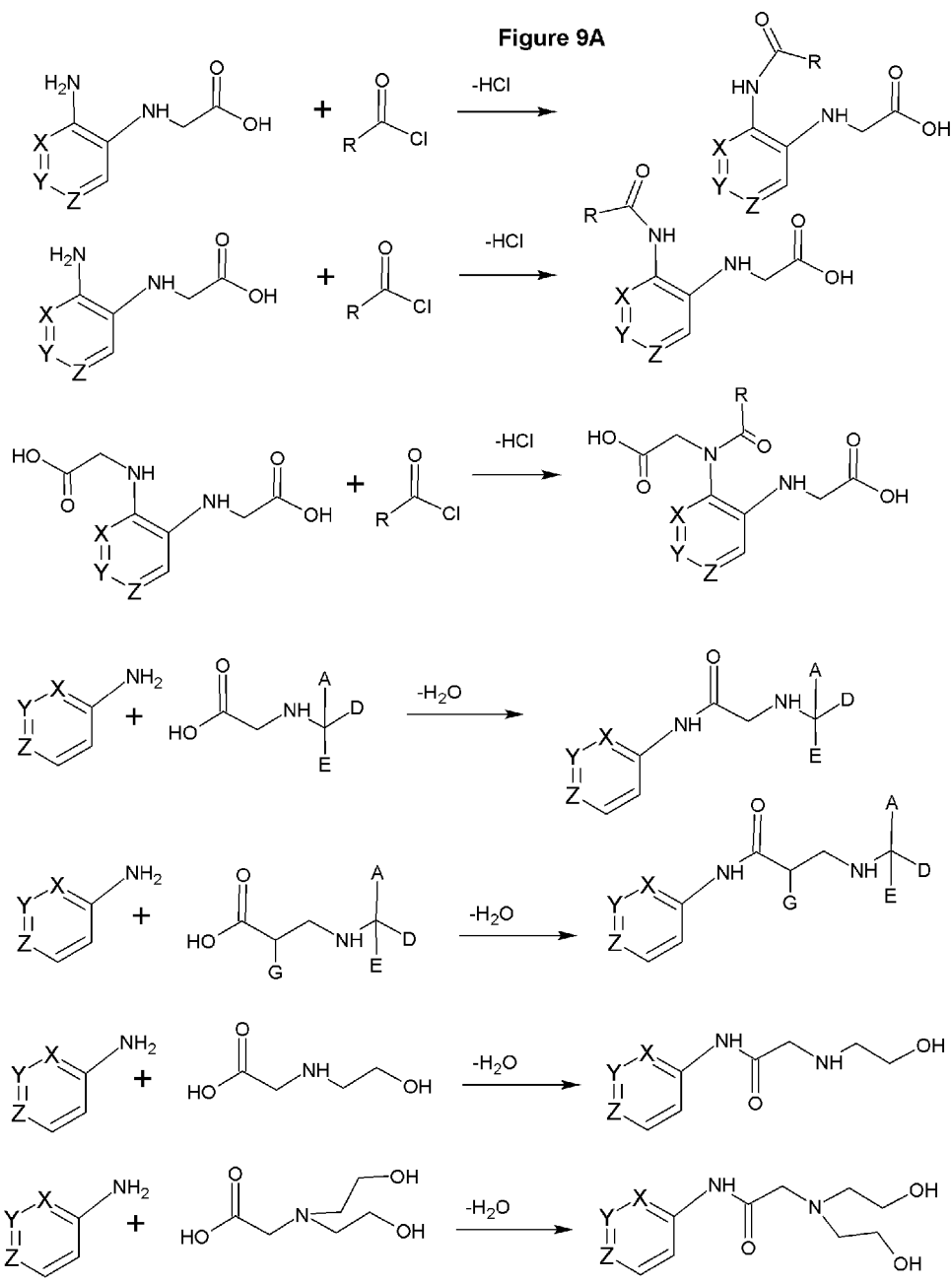
FIGS. 9A-9B show the synthesis of alkyl amides of 3,4-aminopyridine.
Figure 9B:
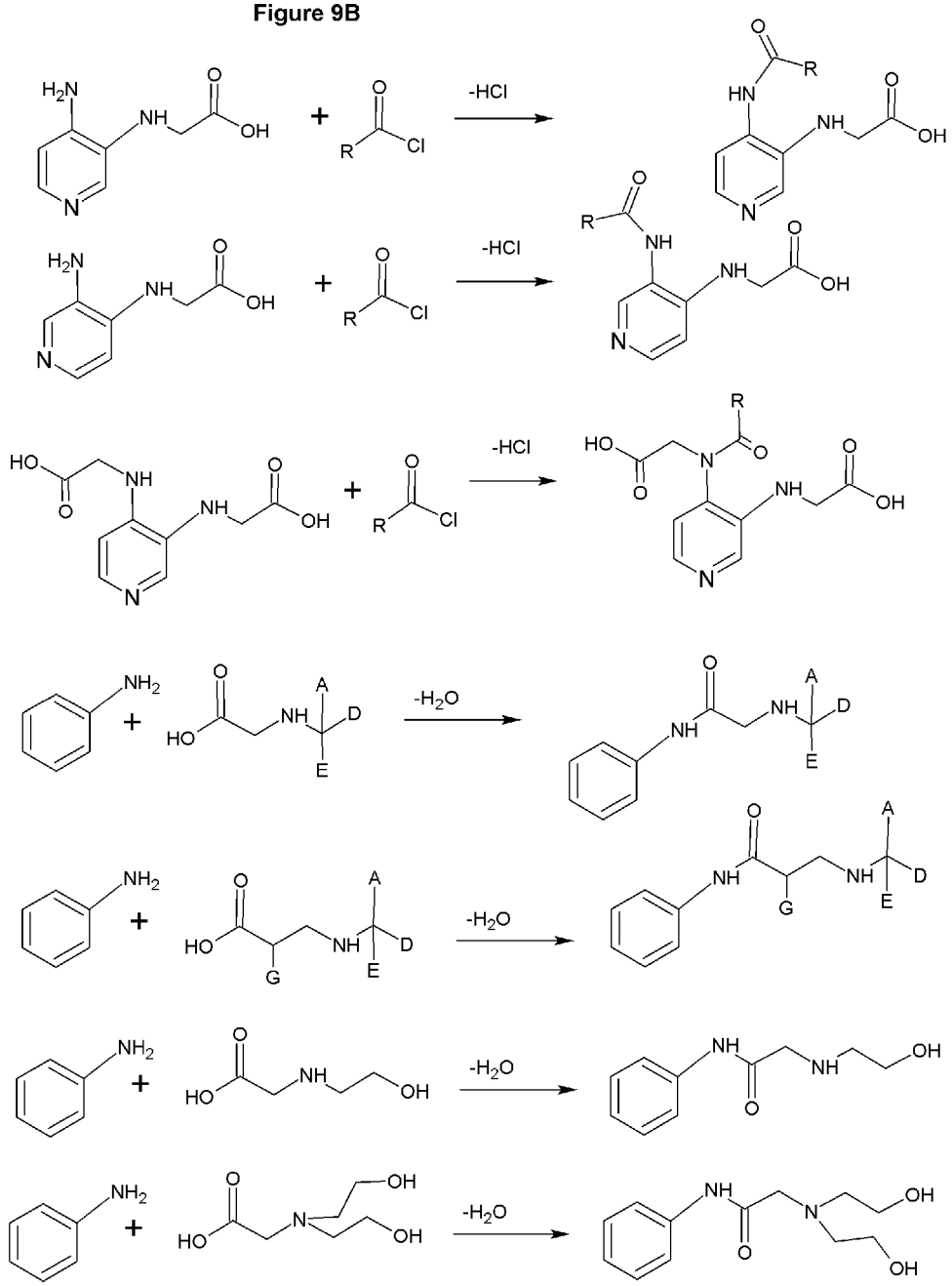

FIGS. 9A-9B teach the addition of an acid chloride to form an amide group to the zwitterionic buffers. The addition of the acid chloride to form the amide allows for the adjustment of water solubility and blood brain barrier penetration. R is any alkyl chain, linear or branched, saturated or unsaturated, cyclic or acyclic. A second, symmetric or asymmetric addition of acid chloride can be made to further enhance the shift in solubility. Also taught are less water soluble amides from aniline.

Figure 10A:
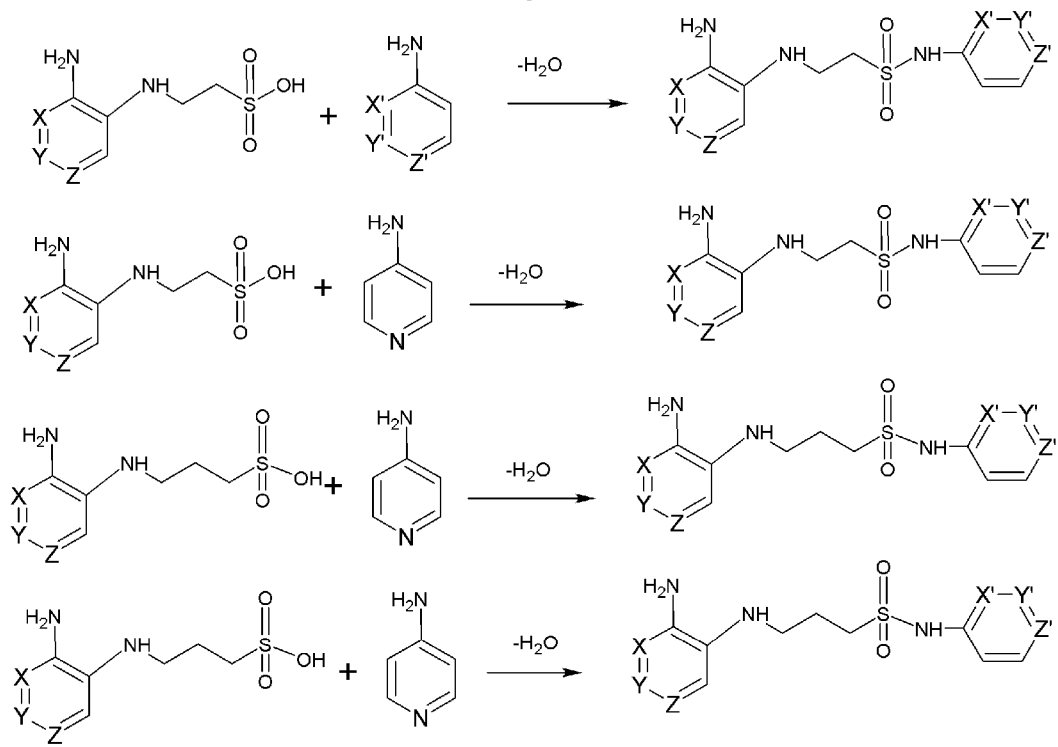
FIGS. 10A-10B teach the synthesis of sulfonamides of 4-aminopyridine.
Figure 10B:
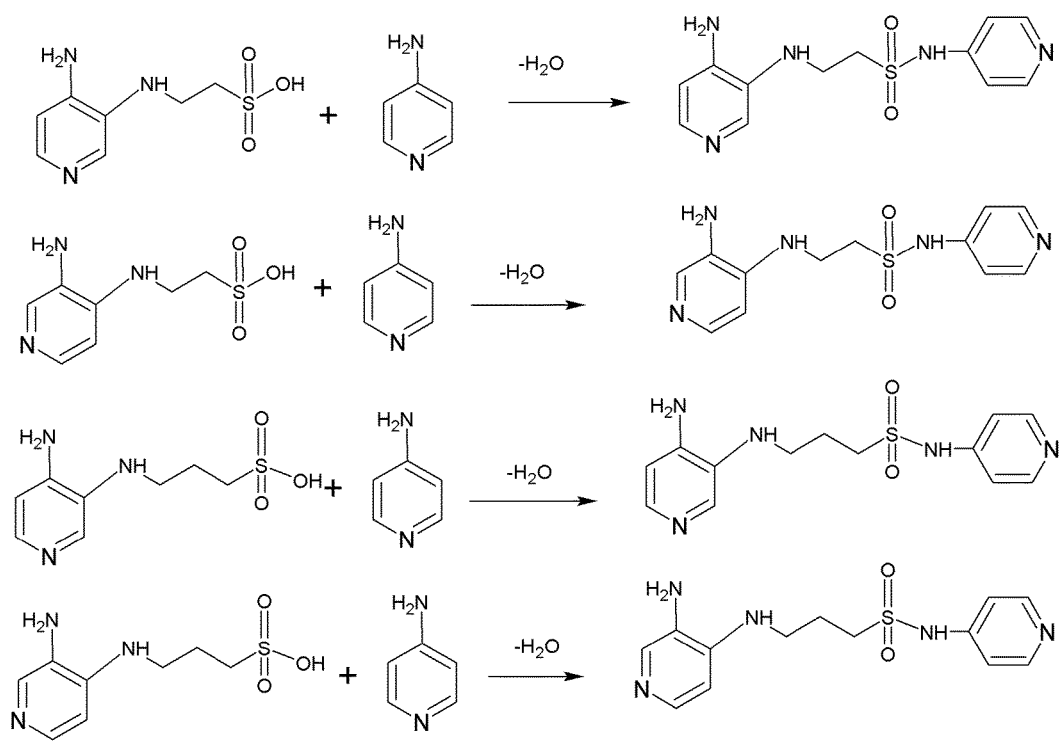

FIGS. 10A-10B teach sulfonamides from the sulfonates of FIGS. 7A-7B and 4-aminopyridine. The sulfonamides of the higher sulfonates from FIGS. 7A-7B are also part of the invention as are the sulfonamides of 2-aminopyridine and 3-aminopyridine in place of 4-aminopyridine. The analogous products where both primary amine groups of 3,4-diaminopyridine are reacted with either sodium vinyl sulfonate or a sultone to make the disulfonate of 3,4-diaminopyridine, can then be made into the corresponding disulfonamide with either 2-aminopyridine, 3-aminopyridine, 4-aminopyridine, 3,4-diaminopyridine or any combination thereof.

One of skill in the art will know that salts include, but are not limited to, sodium, potassium, calcium, transition metals, heavy metals and other cation salts. Salts of any cation inorganic or organic are within the scope of the present invention.

Several descriptions and illustrations have been presented to enhance understanding of the present invention. One skilled in the art will know that numerous changes and variations are possible without departing from the spirit of the invention. Each of these changes and variations are within the scope of the present invention.

I claim:

1. The myelin disease therapy and its salts of the following structure:

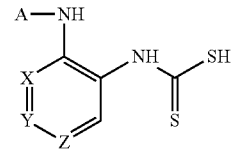

where X,Y, and Z are independently chosen from C or N, where at least one of X, Y or Z is N, and A is chosen from —H, or —CS$_2$H.

2. The myelin disease therapy and its salts of claim 1 where X=Y=C, Z=N, A=—H.

3. The myelin disease therapy and its salts of claim 1 where X=Z=C, Y=N, A=—H.

4. The myelin disease therapy and its salts of claim 1 where X=Y=C, Z=N, A=—CS$_2$H.

5. The myelin disease therapy and its salts of claim 1 where X=Z=C, Y=N, A=—CS$_2$H.

6. The antibiotic of the following structure:

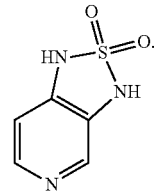

7. The antibiotic of the following structure:

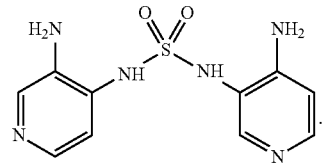 [SMILES: Nc1cnccc1NS(=O)(=O)Nc1cnccc1N]

8. The myelin disease therapy and its salts of claim 1 where Y=Z=C, X=N, A=—H.

9. The myelin disease therapy and its salts of claim 1 where Y=Z=C, X=N, A=—CS$_2$H.

* * * * *